(12) United States Patent
Wise et al.

(10) Patent No.: US 7,303,894 B2
(45) Date of Patent: Dec. 4, 2007

(54) DETECTION OF PHENOLS USING ENGINEERED BACTERIA

(75) Inventors: Arlene A. Wise, Philadelphia, PA (US); Cheryl R. Kuske, Los Alamos, NM (US); Thomas C. Terwilliger, Santa Fe, NM (US)

(73) Assignee: Los Alamos National Security, Los Alamos, NM (US)

( * ) Notice: Subject to any disclaimer, the term of this patent is extended or adjusted under 35 U.S.C. 154(b) by 419 days.

(21) Appl. No.: 10/665,455

(22) Filed: Sep. 18, 2003

(65) Prior Publication Data

US 2005/0260602 A1    Nov. 24, 2005

Related U.S. Application Data

(62) Division of application No. 09/520,538, filed on Mar. 8, 2000, now Pat. No. 6,773,918.

(60) Provisional application No. 60/123,659, filed on Mar. 9, 1999.

(51) Int. Cl.
  C12Q 1/02     (2006.01)
  C12N 1/21     (2006.01)
  C12N 15/00    (2006.01)
  C12N 15/74    (2006.01)
  C12N 15/87    (2006.01)
  C12Q 1/00     (2006.01)
  C12Q 1/66     (2006.01)
  C12P 19/34    (2006.01)

(52) U.S. Cl. .............. 435/29; 435/252.3; 435/252.33; 435/252.34; 435/440; 435/91.2; 435/471; 435/463; 435/8; 435/4; 530/350; 536/23.1

(58) Field of Classification Search ............. 435/440, 435/252.3, 252.33, 252.34, 29, 91.2, 471, 435/463, 8, 4; 530/350; 536/23.1
See application file for complete search history.

(56) References Cited

U.S. PATENT DOCUMENTS 5,837,458 A    11/1998    Minshull et al. .............. 435/6

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Sousa et al., Microbiology 148(Pt5):1291-1303, 2002.*
Pavel et al., J. Bacteriol. 176(24):7550-7557, 1994.*
Shingler and Moore, 1994, J Bacteriology, 176:1555.
Elliot, 1992 J. Bacteriol. 174:245.
Casadaban, 1976 J. Mol. Biol. 104:541.
Simons et al., 1987 Gene 53:85.
Lee, et al., 1990 Biotechniques 9:676.
Dower et al., 1988 Nucleic Acids Res. 16:6127.
Schirmer et al., 1997 J. Bacteriology, 179:4:1329.
Ng et al., 1995, J. Bacteriology, vol. 177, No. 6:1485.
Willardson et al., 1998, Applied and Environmental Microbiology, vol. 64, No. 3:1006.
Cadwell and Joyce, "Mutagenic PCR" in *PCR Primer, a Laboratory Manual*, pp. 583-589, Cold Spring Harbor Laboratory Press, 1995, Diffenbach and Dveksler Ed.
Burchhardt et al., 1997, Mol. Gen. Genet. 254:539.
Byrne and Olsen, 1996, J. Bacteriology, 178:21:6327.
Stemmer, 1994, Nature 370:389.
Branden and Tooze, *Introduction to Protein Structure*, 1991: 247.
Seffernick et al., J. Bacteriology, Apr. 2001, 2405.
Witkowski et al., Biochemistry 1999, 38, 11643.
Wise and Kuske, Applied Molecular Microbiology, Jan. 2000, 163.

* cited by examiner

*Primary Examiner*—Delia M. Ramirez
(74) *Attorney, Agent, or Firm*—Kenneth K. Sharples

(57) ABSTRACT

Detection of phenols using engineered bacteria. A biosensor can be created by placing a reporter gene under control of an inducible promoter. The reporter gene produces a signal when a cognate transcriptional activator senses the inducing chemical. Creation of bacterial biosensors is currently restricted by limited knowledge of the genetic systems of bacteria that catabolize xenobiotics. By using mutagenic PCR to change the chemical specificity of the *Pseudomonas* species CF600 DmpR protein, the potential for engineering novel biosensors for detection of phenols has been demonstrated. DmpR, a well-characterized transcriptional activator of the P. CF600's dmp operon mediates growth on simple phenols. Transcription from Po, the promoter heading the dmp operon, is activated when the sensor domain of DmpR interacts with phenol and mono-substituted phenols. By altering the sensor domain of the DmpR, a group of DmpR derivatives that activate transcription of a Po-lacZ fusion in response to eight of the EPA's eleven priority pollutant phenols has been created. The assays and the sensor domain mutations that alter the chemical specificity of DmpR is described.

1 Claim, 7 Drawing Sheets

DETECTION OF PHENOLS USING ENGINEERED BACTERIA

CROSS-REFERENCE TO RELATED APPLICATIONS

This application is a Divisional of U.S. patent application Ser. No. 09/520,538, filed Mar. 8, 2000, now U.S. Pat. No. 6.773,918, which claims the benefit of United States provisional patent application No. 60/123,659 filed Mar. 9, 1999.

This invention was made with government support under Contract No. W-7405-ENG-36 awarded by the U.S. Department of Energy to The Regents of The University of California. The government has certain rights in the invention.

FIELD OF THE INVENTION

The present invention relates generally to the detection of organic pollutants and, more particularly, to the mutagenic generation of a group of DmpR protein derivatives with improved ability to activate transcription of a reporter gene in bacteria in the presence of phenols, including certain disubstituted phenols, in liquids and soils.

BACKGROUND OF THE INVENTION

In the last three decades, there has been a significant increase in government regulations that hold industrial entities accountable for the chemical pollution that results from their manufacturing activities. In order to comply with environmentally sensitive regulations, businesses must be able to identify contamination and monitor its remediation processes. The cost and technical complexity of chromatographic methods currently in use may act to limit characterization of contaminated sites. One way to lower the cost of detection is to use biosensors derived from genetic systems of bacteria that have evolved to use organic contaminants as growth substrates.

Certain strains of soil bacteria have evolved the capacity to use toxic organic chemicals as food sources. Production of the required metabolic enzymes is, in some cases, controlled by a particular type of regulatory protein that detects the toxic chemical through a direct physical interaction. The protein-chemical complex binds to a cognate promoter sequence and activates expression of genes encoding the required metabolic enzymes. This type of regulatory protein can be utilized as a pollution detecting component in bacteria that have been engineered to signal the presence of environmental pollution.

The most basic whole cell bacterial biosensors are created by placing a reporter gene under control of an inducible promoter. Expression of the reporter gene provides a measurable signal when the appropriate transcription activator protein interacts with an effector chemical.

Phenol and various substituted phenols are used in the manufacture of dyes, photographic chemicals, pesticides, lumber preservatives, microbiocides and herbicides. Current methods for detecting phenol contaminants include gas chromatography and high-pressure liquid chromatography. These chromatographic methods require expensive equipment and highly trained technicians. In response to the U.S. Environmental Protection Agency having listed eleven phenols as priority pollutants, industries that use phenol and phenol derivatives require simple and inexpensive detection methods to identify spills, leaks, and other phenol contamination that result from their manufacturing and service activities.

The construction of bacterial biosensors is limited by the restricted availability of bacteria that are known to metabolize a chemical of interest and, in particular, by the absence of knowledge concerning the genetic systems that control bacterial response to the chemical. Fortunately, some of the bacterial genetic systems that support metabolism of polluting chemicals show significant genetic relatedness. Operons encoding genes required for metabolism of phenol, toluene, benzene, and xylene in some *Pseudomonas* and *Acinetobacter* species are headed by promoters recognized by sigma-54-associated RNA polymerase. Transcription directed by these promoters occurs when the system's regulatory protein detects the presence of the substrate for the catabolic enzymes. Proteins in this category include DmpR, XylR, MopR, PhhR, PhlR, and TbuT. These six proteins show significant similarity to one another at the amino acid level. Sequence information and domain swapping experiments indicate that the general arrangement of these regulatory proteins consists of discrete areas with three independent functions including chemical detection, polymerase activation, and DNA-binding.

XylR and DmpR are the most studied members of this group of transcription activators. The *Pseudomas putida* XylR has already served as the detection component for a number of biosensors based on its ability to activate transcription in response to xylene, toluene and benzene. DmpR, the product of the *Pseudomonas* CF600 dmpR gene, mediates expression of the dmp operon to allow growth on simple phenols. Transcription from Pdmp, the promoter heading the dmp operon, is activated when DmpR senses the presence of phenol, cresols, mono-chlorinated phenols, and some monomethylated phenols (See, e.g., V. Shingler and T. Moore, "Sensing of aromatic compounds by the DmpR transcriptional activator of phenol-catabolizing *Pseudomonas* sp. strain CF600", J. Bacteriol. 176:1555-1560 (1994)). Disubstituted phenols, such as 2,4-dichlorophenol or 2,4-dimethylphenol, are inferior inducers of dmp transcription.

Domain swapping experiments to form XylR-DmpR hybrids demonstrated that the sensor activity of these regulatory proteins is localized to the amino terminal region.

By switching the first 234 amino acids of DmpR with those from XylR, Shingler and Moore, supra, created a chimeric protein that activated transcription from Pdmp in response to toluene and xylene, but not phenol or cresol. The results of the hybrid protein experiments indicated that transcription from Pdmp depends on a direct physical interaction between the sensor domain of DmpR and the inducing phenol.

The single regulatory protein, and the independent domain arrangement of DmpR and other proteins of this type make them particularly suitable candidates for genetic manipulation and suggests a way around the restrictions imposed by limited information about the genetics that control bacterial degradation of xenobiotics. Such altered proteins have the potential to extend the chemical target range of biosensors beyond that based on natural systems.

Therefore, it is an object of the present invention to alter the chemical sensing domain of the protein DmpR to respond to phenol and phenol derivatives which are poorly detected or undetected by the wild type protein.

Another object of the invention is to alter the chemical sensing domain of the protein DmpR to respond to phenol and phenol derivatives without disturbing its transcription activating functions.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for enhancing bacterial response to organic molecules, where the bacteria have a regulatory protein with discrete functional domains for independent activities, one such domain being a sensor domain that detects the organic molecules through a direct physical interaction forming a protein-molecule complex which binds to a cognate promoter sequence and activates expression of genes encoding metabolic enzymes, includes modifying the sensor domain of the regulatory protein such that the response to the organic molecule is enhanced without altering the other domains.

Benefits and advantages of the present invention include the creation of a large variety of engineered proteins with abilities to detect toxic organic chemicals. Such engineered proteins will be useful in development of environmentally beneficial tools that both detect and degrade polluting chemicals.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings:

FIG. 2a shows the results of a β-galactosidase assay for the detection of 2-chlorophenol, while

FIG. 3a shows assays comparing wild type DmpR and DmpR-B23 as detectors for six concentrations of 2-chlorophenol after a 60 minute exposure, while

FIG. 4a shows that a four-hour exposure to phenols increases the detection signal (in β-galactosidase activity units) for low concentrations of 2-chlorophenol for DmpR-B23, whereas

DETAILED DESCRIPTION

Briefly, the present invention includes a method for creating mutant DmpR derivatives having increased response to phenol and substituted phenols. These mutant derivatives are shown to activate the transcription of a reporter gene in the presence of the seven phenols listed as priority pollutants by the U.S. Environmental Protection Agency. Codon changes, including three silent mutations, that improve DmpR's ability to detect disubstituted phenols including 2,4-dichlorophenol and 2,4-dimethylphenol are described for both liquid and soil assays. Additionally, the mutations improve the ability of DmpR to detect di-substituted 4-chloro-3-methyl phenol and mono-substituted 2-chlorophenol, 2-nitrophenol, and 4-nitrophenol. Regulatory proteins capable of detecting organic contaminants through a specific physical interaction have been identified in some *Pseudomonas* and *Acinetobacter* species. Proteins of this type include DmpR, XylR, MopR, PhhR, PhlR, and TbuT. The general arrangement of these proteins consists of discrete functional domains with independent activities. The highly conserved carboxyl and middle regions of these proteins contain regions dedicated to DNA-binding and transcription activation. The less-conserved amino terminal region is known as the sensor domain and is the portion of the protein that physically interacts with (detects) a specific chemical. For example, DmpR, MopR, PhhR, and PhlR detect phenol and activate production of enzymes that metabolize phenol. Chemicals detected by XylR and TbuT include toluene and xylene.

Because of their distinct functional domain organization, proteins of this kind are particularly suitable to genetic modification. A key element in the present invention is the mutagenic modification of DNA corresponding to a protein's sensor domain because this region can be mutagenized without changing the protein's ability to bind DNA and activate gene expression from its cognate promoter. Modification of a sensor domain has potential for creating novel proteins with altered or improved chemical detection ability.

Mutations in the sensor domain of DmpR were generated through mutagenic PCR. Engineered genes were transformed into bacterial test strains that carried DmpR's cognate promoter fused to a reporter gene. This test strain allowed identification and characterization of novel versions of DmpR with chemical detection capabilities that significantly differ from that of the wild type protein. Engineered derivatives of DmpR detect 2,4-dichlorophenol and 2,4-dimethylphenol, as well as other phenolic molecules that are not detected by wild type DmpR.

Figure 1:
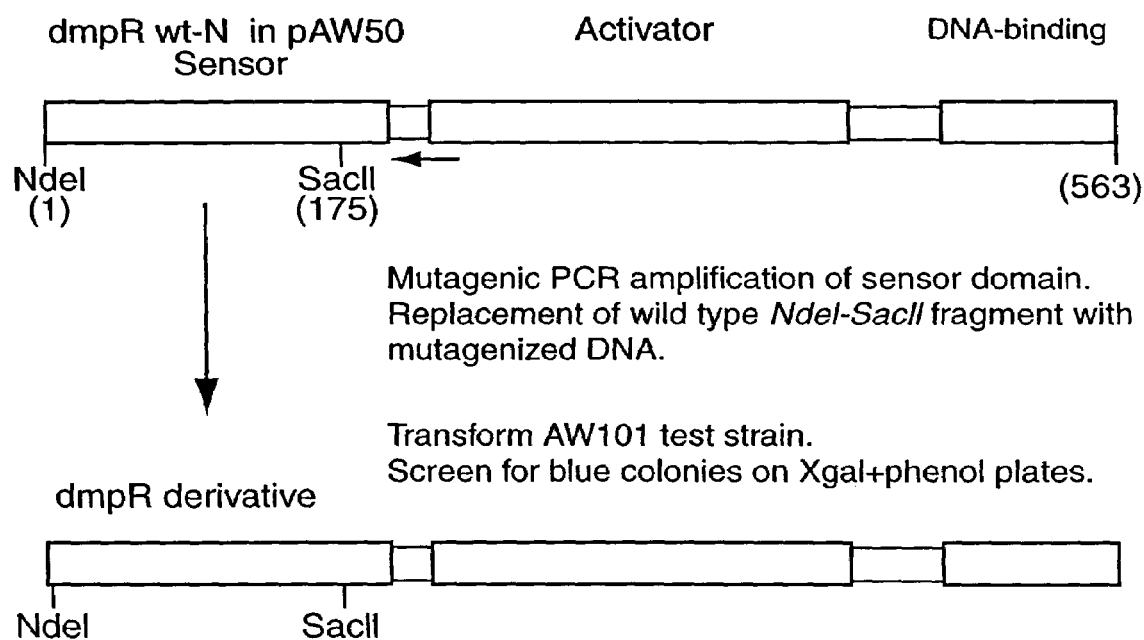
FIG. 1 shows the organization of the DmpR protein and illustrates the domains having distinct functions which made it possible to modify the protein's sensor domain to change its capacity for interacting with a particular phenol without destroying its ability to bind DNA and activate transcription form its cognate promoter Pdmp.

Reference will now be made in detail to the present preferred embodiments of the present invention, examples of which are shown in the accompanying drawings. Turning now to FIG. 1, the dmpR wt-N gene (See, e.g., Shingler and Moore, supra) carried on plasmid pAW50 served as the template for amplification of the dpmR sensor domain by mutagenic polymerase chain reaction (PCR). The products resulting from the mutagenic PCR were digested using NdeI and SacII and ligated back into a pAW50 plasmid fragment, from which the wild type NdeI-SacII region had been removed. This procedure resulted in replacement of DNA corresponding to the first 175 amino acids of DmpR (about 85% of the sensor domain). Ligation products were electroporated into AW101 (trp::Pdmp-lacZ fusion). Transformants were initially selected for tetracycline resistance and then replicated onto plates containing X-gal and one of the test phenols. Colonies that developed more blue color than colonies containing wild type DmpR were selected for further analysis with liquid β-galactosidase assays. β-galactosidase activity is proportional to transcription of the Pdmp-lacZ reporter fusion and is, therefore, a measure of particular variant DmpR's ability to detect phenol or specific substituted phenols. This mutagenic procedure led to the identification of more than twenty DmpR derivatives with altered response to phenols. Five of these derivatives are representative of proteins which show significant promise as effective detectors of phenols listed as primary pollutants by the U.S. Environment Protection Agency.

Having generally described the invention, the following EXAMPLE provides additional details.

EXAMPLE

A. Bacterial strains and plasmids. *E. coli* TE2680 (Elliot, T. 1992. "A method for constructing single-copy lac fusions in *Salmonella typhimurium* and its application to the hemA-prfA operon," J. Bacteriol. 174:245-253) was used as an intermediate strain for placing the Pdmp-lacZ fusion into the chromosome of *E. coli* MC4100 (Casadaban, M. 1976. "Transposition and fusion of the lac genes to selected promoters in *Escherichia coli* using bacteriophage, lambda and Mu," J. Mol. Biol. 104:541-555) to create the dmpR test strain AW101. DH5α (Sambrook, J. E. F. Fritsch, and T. Maniatis. 1989. *Molecular Cloning: A Laboratory Manual*, 2nd Edition. Cold Springs Harbor Laboratory Press. Plainview, N.Y.) was host for plasmid constructions.

pVI401 (See, e.g., Shingler and Moore, supra) served as the source of both the dmpR wt-N gene and the Pdmp promoter which heads the divergently transcribed dmp operon. dmpR wt-N contains a synthetic NdeI restriction site resulting from nucleotide changes immediately upstream from the ATG initiation codon. The coding region of dmpR wt-N remains the same as that of wild type dmpR and the response of the encoded protein to aromatic chemicals is indistinguishable from that produced from the wild type dmpR gene (Shingler et al, supra).

pRS551 (Simons, R. W., F. Houman, and N. Kleckner. 1987. "Improved single and multicopy lac-based cloning vectors for protein and operon fusions," Gene 53:85-96.), a promoter assay vector, contains homology to the engineered trp operon of strain TE2680 and thus, allows integration of promoter-lacZ fusions into the *E. coli* chromosome. pAW51 is a derivative of pRS551 that carries the dmp operon promoter Pdmp on a 0.6 kb DNA fragment fused to the pRS551 lacZ reporter gene.

pAW50 was derived from pBR322 (New England Biolabs, Beverly, Mass.). Following removal of the pBR322 NdeI site, a 2.4 kb NotI fragment containing dmpR wt-N was cloned into a NotI linker which replaced the ScaI site normally located in the ampicillin resistance gene of pBR322. An EcoRI restriction digest followed by ligation removed the promoter of the ampicillin resistance gene, as well as the 5' Not I site. pAW50 contains dmpR sequences extending approximately 650 base pairs upstream from the dmpR translation initiation site.

B. Genetic techniques. Plasmid DNA was isolated using a Qiagen Plasmid Kit (Qiagen, Inc., Chatsworth, Calif.) or by a mini-prep alkaline lysis method (Lee, S-y, and S. Rasheed. 1990. "A simple procedure for maximum yield of high-quality plasmid DNA," Biotechniques 9:676-679). Standard methods were used for restriction digests, gel electrophoresis and ligations. Transformation of *E. coli* was done by the electroporation method (Dower, W. J., J. F. Miller, and C. W. Ragsdale. 1988. "High efficiency transformation of *E. coli* by high voltage electroporation," Nucleic Acids Res. 16:6127-6145) using a Bio-Rad Gene Pulser II unit (Bio-Rad, Hercules, Calif.). Standard PCR to amplify the Po fragment was done as described by Innes et al. (Innes, M. A., D. H. Gelfand, J. J. Sninsky, and T. J. White. 1990. *PCR Protocols: a Guide to Methods and Applications*, Academic Press, New York.).

pVI401 (See, e.g., Shingler and Moore, supra) served as the template for amplifying Po in a reaction that included primers Pdmp5'-EcoRI (5'-CCATCGCTGAATTCTG-CAGCMCAG-3'), SEQ ID No. 8 hereof, and Pdmp3'-BamHI (5'-CGCACACGGATCCMCGAGTGAG-3'), SEQ ID No. 9 hereof. Primers were synthesized on an Applied Biosystems DNA/RNA Synthesizer 394 (Applied Biosystems, Inc. Foster City, Calif.) in the DNA synthesis laboratory of the Life Sciences Division at LANL. PCR was carried out on a Perkin-Elmer 9600 thermal cycler with a 2 minute denaturation step at 92° C. followed by 25 cycles of one minute each at the following temperatures: 92° C., 52° C., and 72° C. The Po PCR product was digested with BamHI and EcoRI to allow directed cloning in front of the promoterless lacZ gene of pRS551 for creation of the Pdmp-lacZ fusion of pAW51.

Mutagenic PCR to change the DmpR sensor domain was done by a modification of Cadwell and Joyce's method (Cadwell, R. C., and G. F. Joyce. 1995. Mutagenic PCR, p. 583-589. In C. W. Dieffenbach and G. S. Dveksler (ed.), PCR Primer, A Laboratory Manual. Cold Spring Harbor Laboratory Press. Cold Spring Harbor, N.Y.). pAW50 served as template in the mutagenic PCR reaction with 25 pmoles each of the following primers: dmpR5'-75 (5'-GCCGTC-GATTGATCATTTGG-3'), SEQ ID No. 10 hereof, and dmpR3'-976, (5'-TGTCCATCATATTGCGCACG-3'), SEQ ID No. 11 hereof. In addition, the reaction contained 5 mM $MgCl_2$, 0.5 mM $MnCl_2$, 0.2 mM dATP and dGTP, 0.8 mM dCTP and dTTP, 10 mM Tris-HCl (pH 8.3), 50 mM KCl, 0.001% (wt/vol) gelatin, and 5 units of AmpliTaq polymerase (Perkin Elmer, Foster City, Calif.). The mutagenic PCR amplification cycle followed a 2 min. denaturation at 92° C. and consisted of 30 cycles of 94° C. (10 s), 56° C. (20 s) and 72° C. (1 min.).

pAW50 and the mutagenized PCR products were each digested with NdeI and SacII. The 525 base pair NdeI-SacII PCR fragment contained most of the dmpR sensor domain. This fragment and pAW50, excluding the wild type sensor domain, were gel purified from low melting point agarose using Elutip-D columns (Schleicher and Schell, Keene, N.H.). The purified DNA fragments served as components in a ligation reaction to reassemble pAW50 derivatives carrying dmpR with variously mutated sensor regions.

C. Test strain construction and screen for sensor domain mutations. pAW51, carrying the Pdmp-lacZ fusion, was linearized through restriction with ScaI, which cuts at a single site within the vector ampicillin resistance gene. The linearized plasmid was then used to transform TE2680 to kanamycin resistance. Transformants were screened for loss of ampicillin and chloramphenicol resistance, a condition indicating integration of the Pdmp-lacZ fusion into the TE2680 chromosome at the trp operon. The general transducing phage P1 kc (American Type Culture Collection, Rockville, Calif.) was used to transfer the fusion to the chromosome of MC4100 resulting in strain AW101.

AW101 was used as a test strain to identify and characterize changes in DmpR's sensing capacity subsequent to sensor domain mutagenesis. pAW50 derivatives were electroporated into AW101 and transformants were selected on Luria-Bertani (Difco, Detroit, Mich.) plates containing 10.5 μg/ml tetracycline. Transformants were then replicaplated onto M9 minimal medium (10) plates containing 0.2% glucose, 30 μg/ml tryptophan, 1 μg/ml thiamine, 10.5 μg/ml tetracycline, 0.25% 5-bromo-4-chloro-3-indoyl-β-D-galactoside (X-Gal), and either no inducer (NI) or 0.05 mM of a phenol derivative. Cells that formed blue colonies on plates containing a phenol derivative were subject to liquid β-galactosidase assays.

D. β-Galactosidase Assays. Overnight cultures of AW101 carrying pAW50 derivatives were diluted 1000-fold into Luria-Bertani broth containing 10.5 μg/ml tetracycline. When cells reached an $OD_{595}$ nm between 0.60 and 0.90 as measured on a Lambda Bio uv/vis spectrophotometer (Perkin Elmer Corp. Analytical Instruments, Norwalk, Conn.), 500 μL samples were pelleted and immediately resuspended in 500 μL spent Luria-Bertani broth containing the appropriate phenol compound. Cell incubation was then continued with shaking at 37° C. for 2 h. Samples were pelleted and frozen at −70° C. for assay the following day.

Liquid β-galactosidase assays were performed using a modification of Miller's assay (Miller, J. H., 1972. "Experiments in Molecular Genetics," Cold Spring Harbor Laboratory, Cold Spring Harbor, N.Y.). Cell sample pellets were thawed and resuspended in Z buffer. The optical density at 595 nm of each cell suspension was read in a microtiter plate using an automated microplate reader (BIO-TEK Instruments, Inc., Winooski, Vt.). Following the addition of 15 μL 0.1% sodium dodecyl sulfate and 25 μL $HCCl_3$, the remaining cell suspension was vortexed for 30 s to lyse cells. The reaction was begun with the addition of 50 μL o-nitrophenyl-β-D-galactopyranoside (2.5 mg/ml) to the lysed cells. Reactions were incubated at 26° C. until stopped with the addition of 50 μL 1M $Na_2CO_3$. Color development of the reactions was read at $OD_{415}$ on the microplate reader. Arbitrary units for graphing purposes were calculated as $(1000 \times OD_{415})/(time)(OD_{595})$ where time is the reaction time in minutes. Equivalent cell volumes were read for both optical densities.

E. DNA Sequencing. Mutations in the dmpR sensor domains carried by pAW50 derivatives were identified using an ABI PRISM Dye Terminator Cycle Sequencing kit and following the manufacturer's (Perkin-Elmer) protocol. Electrophoresis of sequencing reactions was carried out on 4% polyacrylamide gels using an ABI 373A Stretch DNA Sequencer (Applied Biosystems, Inc., Foster City, Calif.). Analysis of mutant sensor domain DNA and amino acid sequences was done using DNASTAR LASERGENE software (DNASTAR Inc., Madison, Wis.).

Figure 2A:
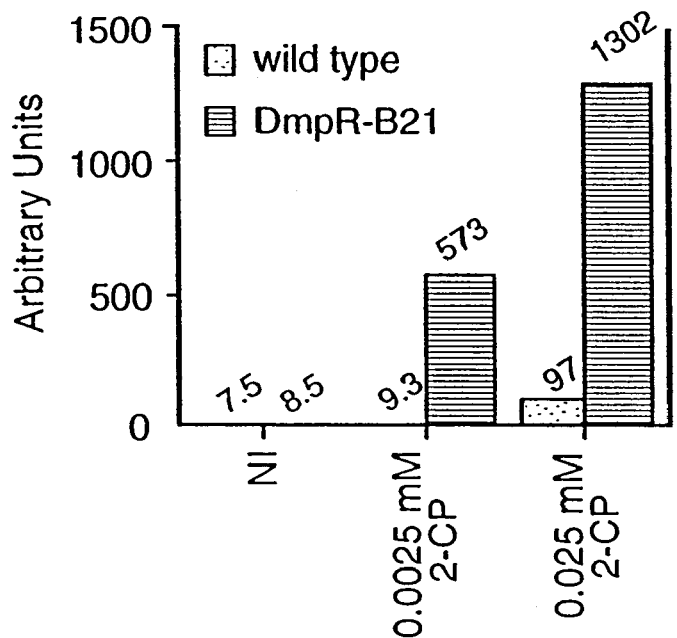
Figure 2B:
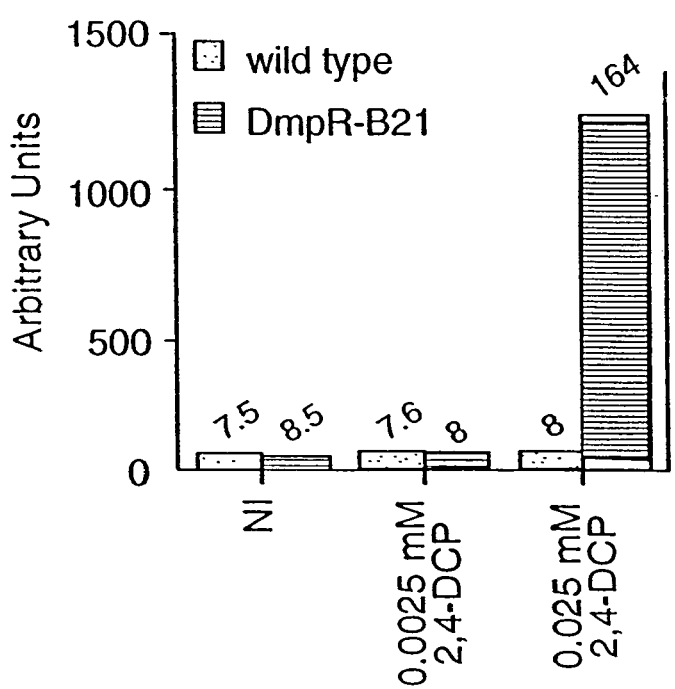
FIG. 2b shows the assay for 2,4-dichlorophenol using the bacterial test strain containing either wild type DmpR or the derivative DmpR-B21, where NI indicates a negative control containing no inducer (no phenol).

FIG. 2a shows the results of a β-galactosidase assay for the detection of 2-chlorophenol, while FIG. 2b shows the assay for 2,4-dichlorophenol using the bacterial test strain containing either wild type DmpR or the derivative DmpR-B21 (SEQ ID No. 3), where NI indicates a negative control containing no inducer (no phenol). For all included graphs, units are β-galactosidase activity normalized for time length of assay and number of cells in assay. NI indicates a negative control containing no inducer (no phenol). Wild type DmpR has no apparent response to a 0.0025 mM solution of 2-chlorophenol (0.3 parts per million), whereas DmpR-B21 responds well with a 60-fold increase in β-galactosidase activity. 2-chlorophenol is a natural inducer of the wild type DmpR protein, as shown by its signal production (97 units) when exposed to a 0.025 mM solution of 2-chlorophenol. A more complex phenol, 2,4-dichlorophenol, elicits a response from DmpR-B21 at 0.025 mM (4 parts per million), but not from the natural DmpR protein. Note changes in axis between graphs.

Figure 3A:
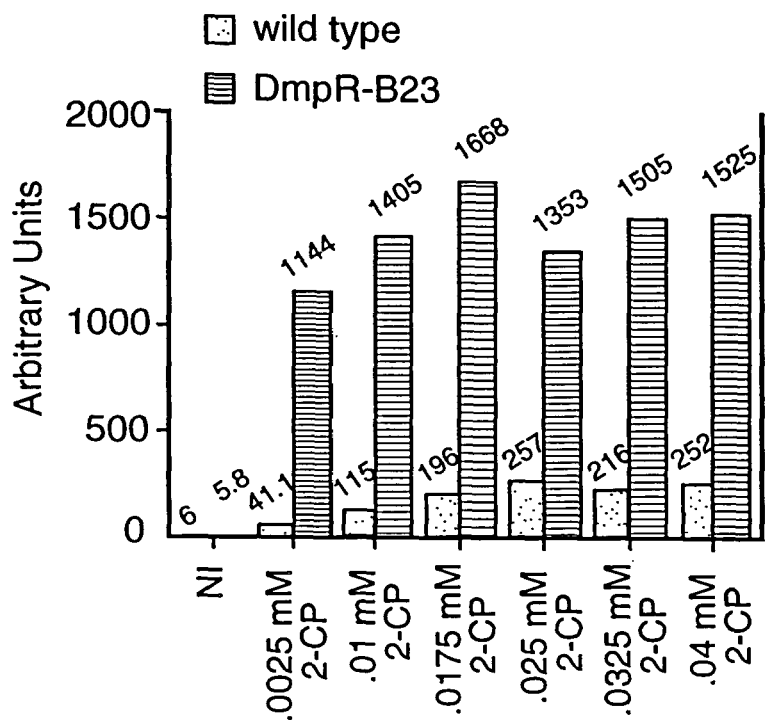
Figure 3B:
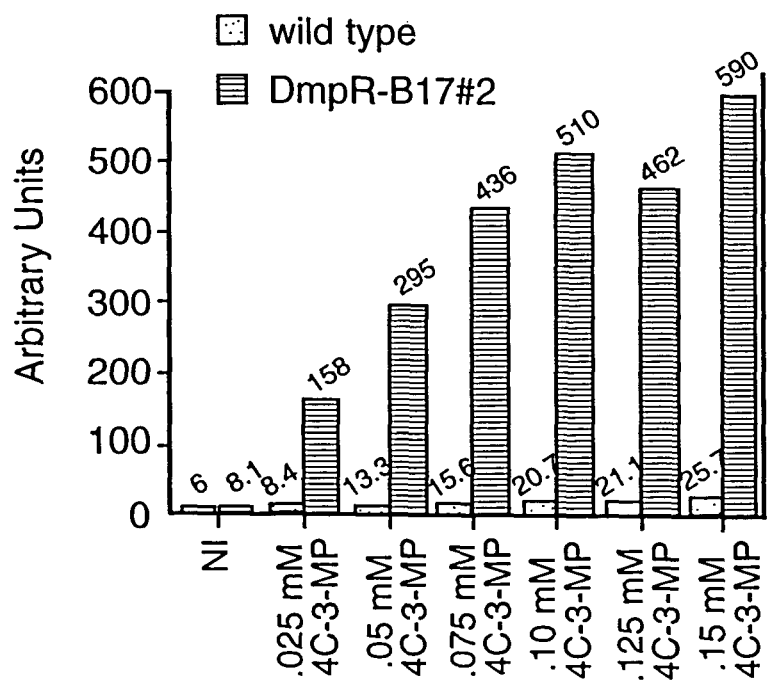
FIG. 3b shows assays comparing the response of wild type DmpR and DmpR-B17#2 to six concentrations of 4-chloro-3-methylphenol.

FIG. 3a shows assays comparing wild type DmpR and DmpR-B23 (SEQ ID No. 4 hereof) as detectors for six concentrations of 2-chlorophenol after a 60 minute exposure, while FIG. 3b shows assays comparing the response of wild type DmpR and DmpR-B17#2 (SEQ ID No. 2 hereof) to six concentrations of 4-chloro-3-methylphenol. Both DmpR-B23 and DmpR-B17#2 are significantly better detectors of substituted phenols than the wild type protein at all concentrations assayed.

Figure 4A:
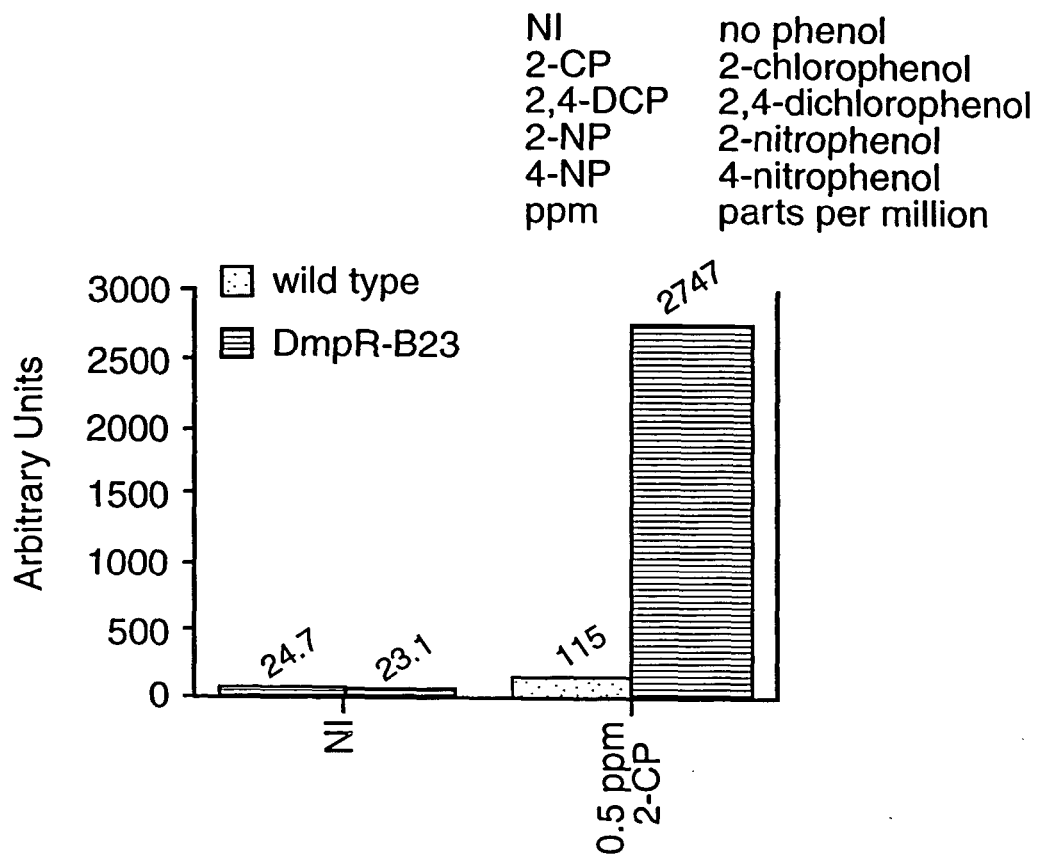
Figure 4B:
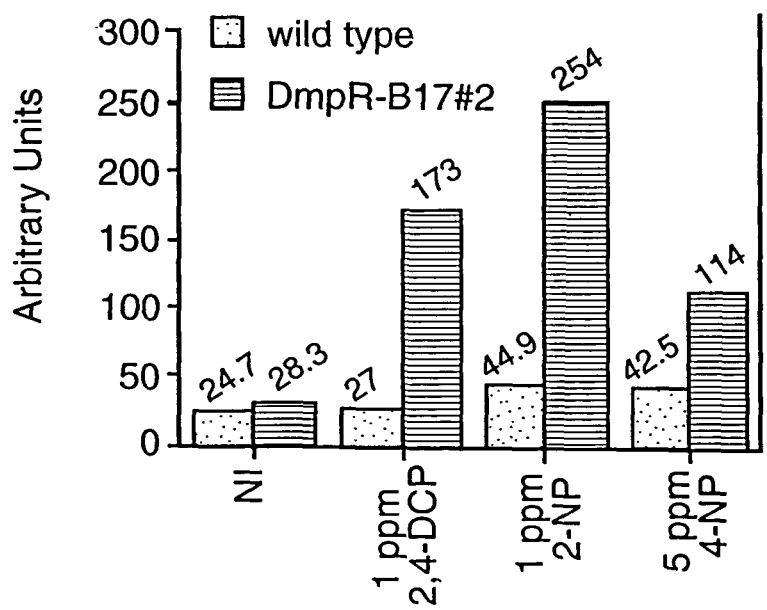
FIG. 4b shows the response of DmpR-B17#2 to low concentrations of 2,4-dichlorophenol, 2-nitrophenol, and 4-nitrophenol.

FIG. 4a shows that a four-hour exposure to phenols increases the detection signal (in β-galactosidase activity units) for low concentrations of 2-chlorophenol for DmpR-B23, whereas FIG. 4b shows the response of DmpR-B17#2 (SEQ ID No. 2 hereof) to low concentrations of 2,4-dichlorophenol, 2-nitrophenol, and 4-nitrophenol. DmpR-B23's response to 0.5 ppm 2-chlorophenol was more than 20-fold higher than that of the wild type DmpR protein. DmpR-B17#2 responds to low concentrations of phenols (2,4-dichlorophenol, 2-nitrophenol, and 4-nitrophenol) that are poor effectors of the wild type DmpR protein.

Figure 5A:
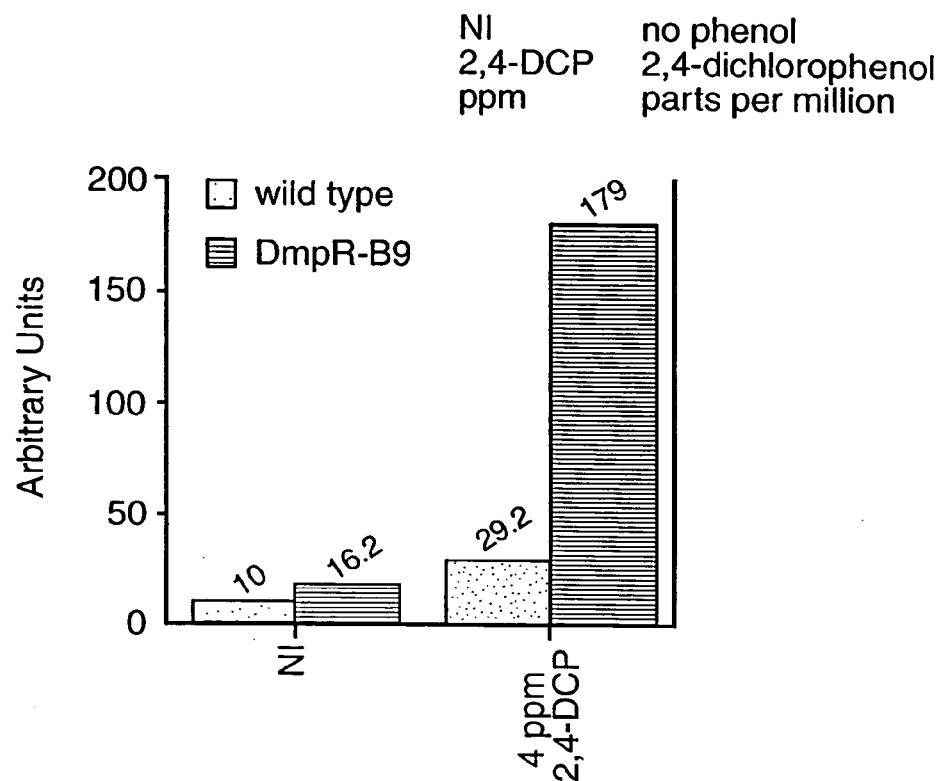
FIG. 5a compares the detection of 2,4-dichlorophenol by DmpR-B9 with that of the wild type DmpR for unsubstituted phenol shown in FIG. 5b in contaminated soil, unsubstituted phenol being a natural effector of wild type DmpR.
Figure 5B:
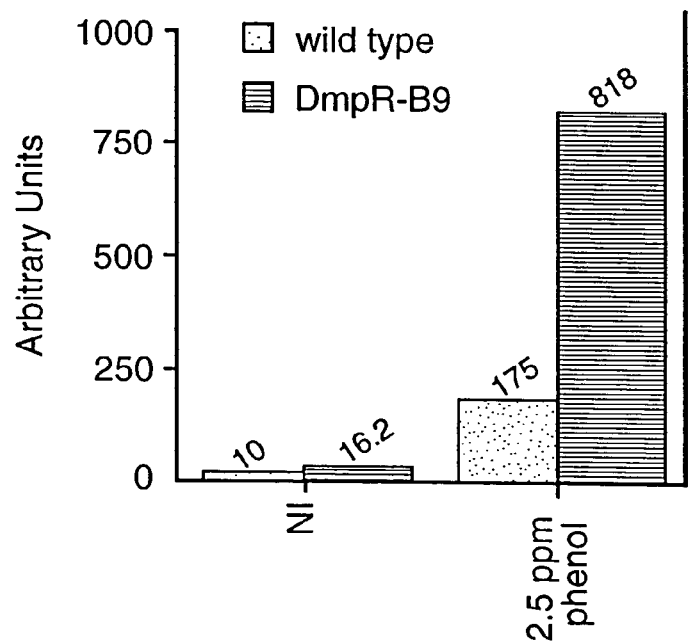

FIG. 5a compares the detection of 2,4-dichlorophenol by DmpR-B9 (SEQ ID No. 1 hereof) with that for unsubstituted phenol shown in FIG. 5b in contaminated soil, unsubstituted phenol being a natural effector of wild type DmpR. Detection of chemicals in contaminated soil is often difficult because soil may bind the phenols, making them less available to the test bacteria. However, DmpR-B9's capacity to detect phenols in soil remains significantly better than that of the wild type protein. The response of DmpR-B9 to 4 parts per million (ppm) 2,4-dichlorophenol in soil is six-fold higher than that of wild type DmpR. DmpR-B9's response to 2.5 ppm phenol is four-fold better than that of wild type.

Figure 6A:
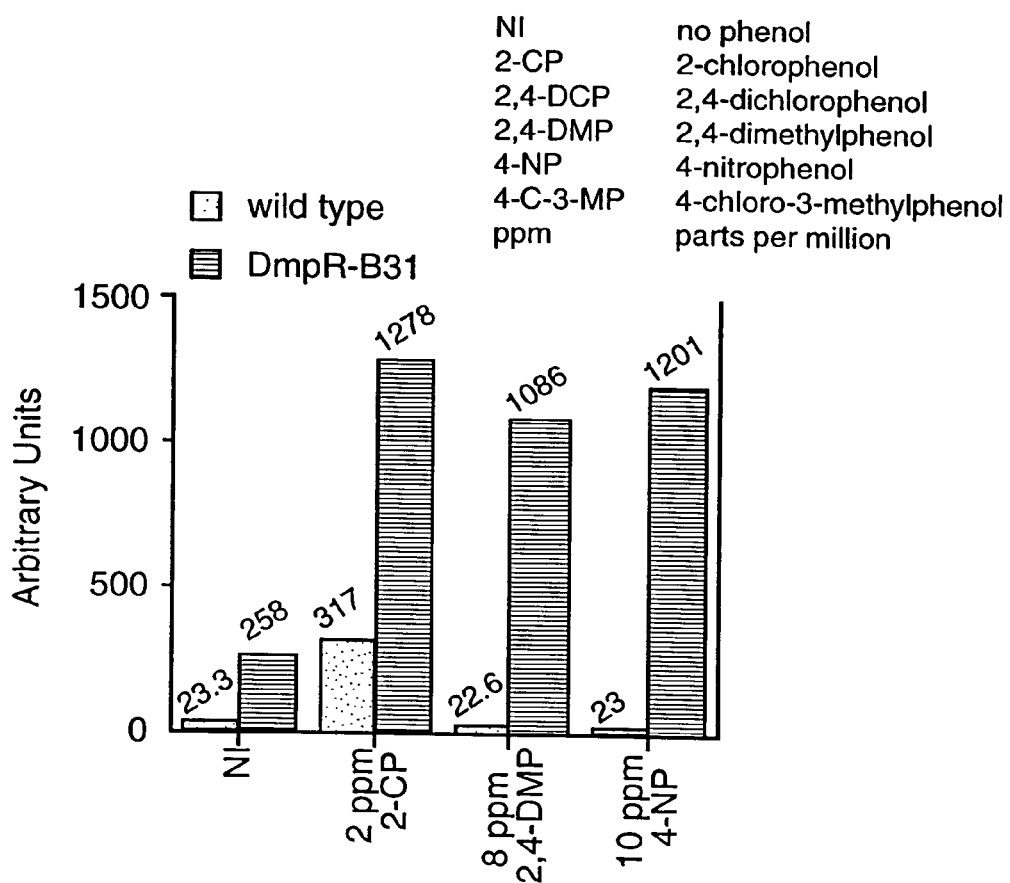
FIG. 6a compares the detection of 2-chlorophenol, 2,4-dimethylphenol, and 4-nitrophenol by wild type DmpR with that for the engineered protein DmpR-B31, while FIG. 6b compares the detection of 2,4-dichlorophenol and 4-chloro-3-methylphenol by the wild type DmpR and DmpR-D12; DmpR-B31 showing a strong response to most substituted phenols, but having a relatively high uninduced (NI) value.
Figure 6B:
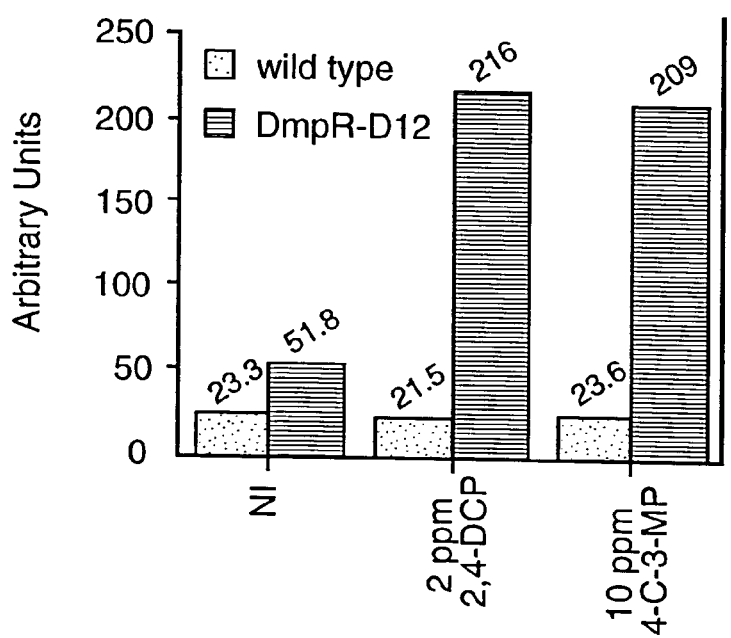

FIG. 6a compares the detection of 2,4-dichlorophenol, 2,4-dimethylphenol, and 4-nitrophenol by wild type DmpR with that for the engineered protein DmpR-B31 (SEQ ID No. 5 hereof), while FIG. 6b compares the detection of 2,4-dichlorophenol and 4-chloro-3-methylphenol by the wild type DmpR and DmpR-D12 (SEQ ID No. 7 hereof). DmpR-B31 shows a strong response to most substituted phenols, but also has a relatively high uninduced (NI) value. DmpR-D12's detection of 10 ppm 4-chloro-3-methylphenol and 3 ppm 2,4-dichlorophenol are eight and 10-fold higher than that of wild type DmpR.

Figure 7A:
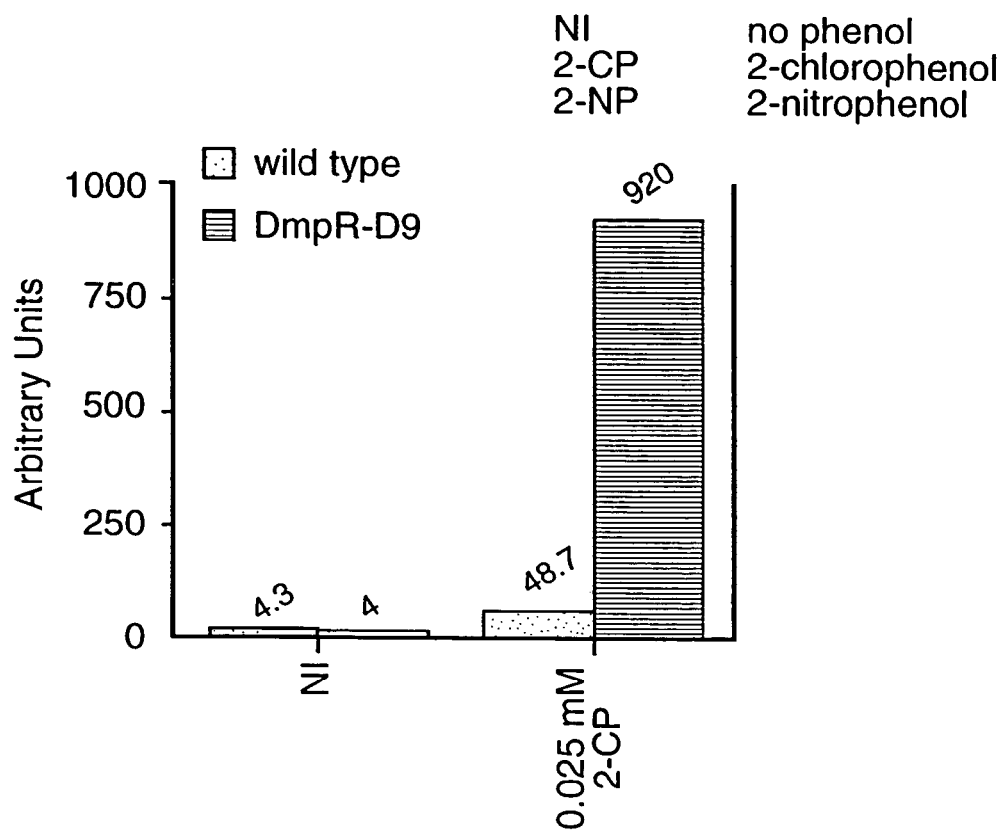
FIG. 7a compares the detection of 2-chlorophenol by DmpR-D9 with its detection by wild type DmpR, while FIG. 7b compares the detection of 2-nitrophenol by DmpR-D9 with that for wild type DmpR.
Figure 7B:
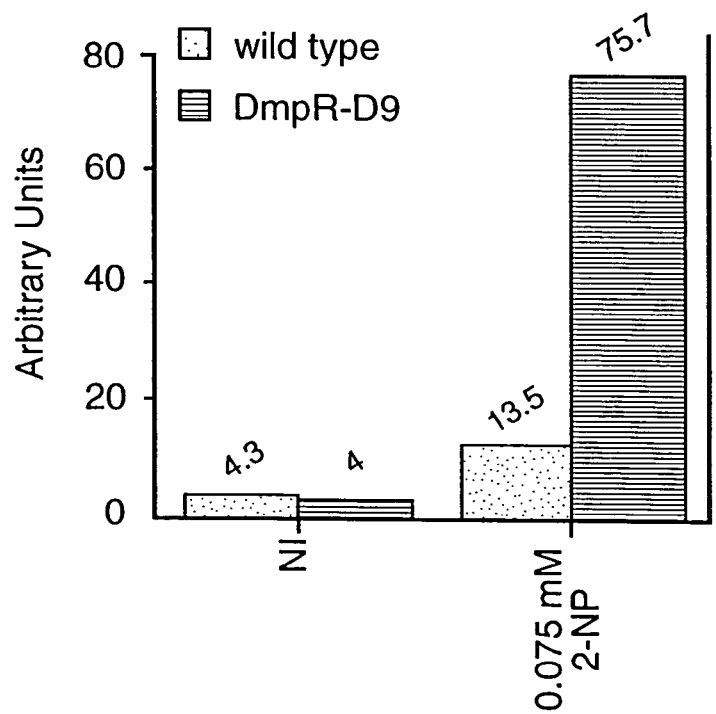

FIG. 7a compares the detection of 2-chlorophenol by DmpR-D9 (SEQ ID No. 6) with its detection by wild type DmpR, while FIG. 7b compares the detection of 2-nitrophenol by DmpR-D9 with that for wild type DmpR. DmpR-D9's response to 2-chlorophenol is nineteen-fold higher than that of the wild type protein, while its response to 2-nitrophenol is five times higher than that of wild type DmpR.

The foregoing description of the invention has been presented for purposes of illustration and description and is not intended to be exhaustive or to limit the invention to the precise form disclosed, and obviously many modifications and variations are possible in light of the above teaching. For example, it would be apparent to one having ordinary skill in the art after reading the present disclosure that mutating the sensor domain to enhance the response of bacteria to selected organic molecules could be achieved by removing the sensor domain from the bacterial DNA encoding the regulatory protein, subjecting the removed sensor domain to gene reshuffling, ligating the mutated sensor domain into the DNA encoding the regulatory protein, and testing the bacteria for enhanced response to the chosen organic molecules. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for detecting 2-chlorophenol or 2,4-dichlorophenol in a test sample, wherein said method comprises the steps of:
   (1) culturing a *Pseudomonas* or *Escherichia coli* cell comprising (a) a reporter gene under the control of the Po promoter inducible by the DmpR protein of *Pseudomonas* sp. strain CF600, and (b) a *Pseudomonas* sp. strain CF600 DmpR gene mutated at the coding region of the sensor domain, wherein the coding region of the sensor domain of the mutated *Pseudomonas* sp. strain 0F600 DmpR gene comprises SEQ ID NO: 3, and wherein said mutation results in enhanced transcriptional activation response to 2-chlorophenol and 2,4-dichlorophenol relative to the response obtained with wild type *Pseudomonas* sp. strain CF600 DmpR protein; and,
   (2) detecting the expression of the reporter gene, wherein expression of the reporter gene is indicative of the presence of 2-chlorophenol or 2,4-dichlorophenol.

* * * * *

SEQUENCE LISTING

<160> NUMBER OF SEQ ID NOS: 17

<210> SEQ ID NO 1
<211> LENGTH: 540
<212> TYPE: DNA
<213> ORGANISM: Pseudomonas sp. CF600

<400> SEQUENCE: 1

```
atgccgatcg agtacaagcc tgaaatccag cactccgatt tcaaggacct gaccaacctg      60
atccacttcc agagcatgga aggcaagatc tggcttggcg aacagcgcat gctgttgctg     120
cagtcttcag cgatggccag ctttcgccgg gaaatggtca ataccctggg catcgaacgc     180
gccaagggct tgttcctgcg ccatggttac cagtccggcc tgaaggatgc cgaactggcc     240
aggaagctga gaccgaatgc cagcgaagtc ggcatgttcc tcgctgggcc gcagatgcat     300
tcactcaagg gtctggtcaa ggtccgcccc accgagctcg atatcgacaa ggaatacggg     360
cgcttctatg ccgagatgga gtggatcgac tggttcgagg tggaaatctg ccagaccgac     420
ctggggcaga tgcaagaccc ggtgtgctgg actgtgctcg gctacgcctg cgcctattcc     480
tcggcgttca tgggccggga aatcatcttc aaggaagtca gctgccgcgg ctgcggcggc     540
```

<210> SEQ ID NO 2
<211> LENGTH: 540
<212> TYPE: DNA
<213> ORGANISM: Pseudomonas sp. CF600

<400> SEQUENCE: 2

```
atgccgatca agtacaagcc tgaaatccag cactccgatt tcaaggacct gaccaacctg      60
atccacttcc agagcatgga aggcaagatc tggcttggcg aacagcgcat gctgttgctg     120
cagttttcgg cgatggccag ctttcgccgg gaaatggtca ataccctggg catcgaacgc     180
gccaagggct tgttcctgcg ccatggttac cagtccggcc tgaaggatgc cgaactggcc     240
aggaagctga gaccgaatgc cagcgaagtc ggcatgttcc tcgctgggcc gcagatgcat     300
tcactcaagg gtctggtcaa ggtccgcccc accgagctcg atatcgacaa ggaatacggg     360
cgcttctatg ccgagatgga gtggatcgac tggttcgagg tggaaatctg ccagaccgac     420
ctggggcaga tgcaagaccc ggtgtgctgg actgtgctcg gctacgcctg cgcctattcc     480
tcggcgttca tgggccggga aatcatcttc aaggaagtca gctgccgcgg ctgcggcggc     540
```

<210> SEQ ID NO 3
<211> LENGTH: 540
<212> TYPE: DNA
<213> ORGANISM: Pseudomonas sp. CF600

<400> SEQUENCE: 3

```
atgccgatca agtacaagcc tgaaatccag cactccgatt tcaaggacct gaccaacctg      60
atccacttcc agagcatgga aggcaagatc tggcttggcg aacaacgcat gctgttgctg     120
cagttttcag cgatggccag ctttcgccgg gaaatggtca ataccctggg catcgaacgc     180
```

```
gccaagggct tgttcctgcg ccatggttac cagtccggcc tgaaggatgc cgaactggcc    240
aggaagctga gaccgaatgc cagcgaagtc ggcatgttcc tcgctgggcc gcagatgcat    300
tcactcaagg gtctggtcaa ggtccgcccc accgggctcg atatcgacaa ggaatacggg    360
cgcttctatg ccgagatgga gtggatcgac tggttcgagg tggaaatctg ccagaccgac    420
ctggggcaga tgcaagaccc ggtgtgctgg actgtgctcg gctacgcctg cgcctattcc    480
tcggcgttca tgggccggga aatcatcttc aaggaagtca gctgccgcgg ctgcggcggc    540
```

<210> SEQ ID NO 4
<211> LENGTH: 540
<212> TYPE: DNA
<213> ORGANISM: Pseudomonas sp. CF600

<400> SEQUENCE: 4

```
atgccgatca agtacaagcc tgaaatccgg cactccgatt tcaaggacct gaccaacctg     60
atccacttcc agagcatgga aggcaagatc tggcttggcg aacagcgcat gctgttgctg    120
cagttttcag cgatggccag cttttcgccg gaaatggtca ataccctggg catcgaacgc    180
gccaagggct tgttcctgcg ccatggttac cagtccggcc tgaaggatgc cgaactggcc    240
aggaagctga gaccgaatgc cagcgaagtc ggcatgttcc tcgctgggcc gcagatgcat    300
tcactcaagg gtctggtcaa ggtccgcccc accgagctcg atatcgacat ggaatacggg    360
cgcttctatg ccgagatgga gtggatcgac tggttcgagg tggaaatctg ccagaccgac    420
ctggggcaga tgcaagaccc ggtgtgctgg actgtgctcg gctacgcctg cgcctattcc    480
tcggcgttca tgggccggga aatcatcttc aaggaagtca gctgccgcgg ctgcggcggc    540
```

<210> SEQ ID NO 5
<211> LENGTH: 540
<212> TYPE: DNA
<213> ORGANISM: Pseudomonas sp. CF600

<400> SEQUENCE: 5

```
atgccgatca agtacaagcc tgaaatccag cactccgatt tcaaggacct gaccaacctg     60
atccacttcc agagcatgga aggcaagatc tggcttggcg aacagcgcat gctgttgctg    120
cagttttcag cgatggccag cttttcgccg gaaatggtca ataccctggg cgtcgaacgc    180
accaagggct tgttcctgcg ccatggttac cagtccggcc tgaaggatgc cgaactggcc    240
aggaagctga gaccgaatgc cagcgaagtc ggcatgttcc ttgctgggcc gcagatgcat    300
tcactcaagg gtctggtcaa ggtccgcccc accgagctcg atatcgacaa ggaatacggg    360
cgcttctatg ccgagatgga gtggatcgac tggttcgagg tggaaatctg ccagaccgac    420
ctggggcaga tgcaaggccc ggtgtgctgg actgtgctcg gctacgcctg cgcctattcc    480
tcggcgttca tgggccggga aatcatcttc aaggaagtca gctgccgcgg ctgcggcggc    540
```

<210> SEQ ID NO 6
<211> LENGTH: 540
<212> TYPE: DNA
<213> ORGANISM: Pseudomonas sp. CF600

<400> SEQUENCE: 6

```
atgccgatca agtacaagcc tgaaatccag cactccgatt tcaaggacct gaccaacctg     60
atccacttcc agagcatgga aggcaagatc tggcttggcg aacagcgcat gctgttgctg    120
cagttttcag cgatggccag cttccgccgg aaatggtca ataccctggg catcgaacgc    180
gccaagggct tgttcctgcg ccatggttac cagtccggcc tgaaggatgc cgaactggcc    240
```

-continued

```
aggaagctga gaccgaatgc cagcgaagtc ggcatgttcc tcgctgggcc gcagatgcat      300
tcactcaagg gtctggtcaa ggtccgcccc accgagctcg atatcggcag ggaatacggg      360
cgcttctatg ccgagatgga gtggatcgac tggttcgagg tggaaatctg ccagaccgac      420
ctggggcaga tgcaagaccc ggtgtgctgg actgtgctcg gctacgcctg cgcctattcc      480
tcggcgctca tgggccggga aatcatcttc aaggaagtca gctgccgcgg ctgcggcggc      540
```

<210> SEQ ID NO 7
<211> LENGTH: 540
<212> TYPE: DNA
<213> ORGANISM: Pseudomonas sp. CF600

<400> SEQUENCE: 7

```
atgccgatca agtacaagcc tgaaatccag cactccgatt tcaaggacct gaccaacctg       60
atccacttcc agagcatgga aggcaagatc tggcttggcg aacagcgcat gctgttgctg      120
cagttttcag cgatggccag cttccgccgg gaaatggtca taccctgggg catcgaacgc      180
gccaagggct tgttcctgcg ccatggttac cagtccggcc tgaaggatgc cgaactggcc      240
aggaagctga gaccgaatgc cagcgaagtc ggcatgttcc tcgctgggcc gcagatgcat      300
tcactcaagg gtctggtcaa ggtccgcccc accgagctcg atatcgacaa ggaatacggg      360
cgcttctatg ccgagatgga gtggatcgac tggttcgagg tggaaatctg ccagaccgac      420
ccggggcaga tgcaagaccc ggtgtgctgg actgtgctcg gctacgcctg cgcctattcc      480
tcggcgttca tgggccggga aatcatcttc aaggaagtca gctgccgcgg ctgcggcggc      540
```

<210> SEQ ID NO 8
<211> LENGTH: 180
<212> TYPE: PRT
<213> ORGANISM: Pseudomonas sp. CF600

<400> SEQUENCE: 8

```
Met Pro Ile Lys Tyr Glu Pro Glu Ile Gln His Ser Asp Phe Lys Asp
1               5                   10                  15

Leu Thr Asn Leu Ile His Phe Gln Ser Met Glu Gly Lys Ile Trp Leu
            20                  25                  30

Gly Glu Gln Arg Met Leu Leu Leu Gln Ser Ser Ala Met Ala Ser Phe
        35                  40                  45

Arg Arg Glu Met Val Asn Thr Leu Gly Ile Glu Arg Ala Lys Gly Leu
    50                  55                  60

Phe Leu Arg His Gly Tyr Gln Ser Gly Leu Lys Asp Ala Glu Leu Ala
65                  70                  75                  80

Arg Lys Leu Arg Pro Asn Ala Ser Glu Val Gly Met Phe Leu Ala Gly
                85                  90                  95

Pro Gln Met His Ser Leu Lys Gly Leu Val Lys Val Arg Pro Thr Glu
            100                 105                 110

Leu Asp Ile Asp Lys Glu Tyr Gly Arg Phe Tyr Ala Glu Met Glu Trp
        115                 120                 125

Ile Asp Ser Phe Glu Val Glu Ile Cys Gln Thr Asp Leu Gly Gln Met
    130                 135                 140

Gln Asp Pro Val Cys Trp Thr Leu Leu Gly Tyr Ala Cys Ala Tyr Ser
145                 150                 155                 160

Ser Ala Phe Met Gly Arg Glu Ile Ile Phe Lys Glu Val Ser Cys Arg
                165                 170                 175

Gly Cys Gly Gly
```

-continued

<210> SEQ ID NO 9
<211> LENGTH: 180
<212> TYPE: PRT
<213> ORGANISM: Pseudomonas sp. CF600

<400> SEQUENCE: 9

Met Pro Ile Lys Tyr Lys Pro Glu Ile Gln His Ser Asp Phe Lys Asp
1               5                   10                  15

Leu Thr Asn Leu Ile His Phe Gln Ser Met Glu Gly Lys Ile Trp Leu
            20                  25                  30

Gly Glu Gln Arg Met Leu Leu Gln Phe Ser Ala Met Ala Ser Phe
        35                  40                  45

Arg Arg Glu Met Val Asn Thr Leu Gly Ile Glu Arg Ala Lys Gly Leu
    50                  55                  60

Phe Leu Arg His Gly Tyr Gln Ser Gly Leu Lys Asp Ala Glu Leu Ala
65                  70                  75                  80

Arg Lys Leu Arg Pro Asn Ala Ser Glu Val Gly Met Phe Leu Ala Gly
                85                  90                  95

Pro Gln Met His Ser Leu Lys Gly Leu Val Lys Val Arg Pro Thr Gly
            100                 105                 110

Leu Asp Ile Asp Lys Glu Tyr Gly Arg Phe Tyr Ala Glu Met Glu Trp
        115                 120                 125

Ile Asp Ser Phe Glu Val Glu Ile Cys Gln Thr Asp Leu Gly Gln Met
    130                 135                 140

Gln Asp Pro Val Cys Trp Thr Leu Leu Gly Tyr Ala Cys Ala Tyr Ser
145                 150                 155                 160

Ser Ala Phe Met Gly Arg Glu Ile Ile Phe Lys Glu Val Ser Cys Arg
                165                 170                 175

Gly Cys Gly Gly
            180

<210> SEQ ID NO 10
<211> LENGTH: 180
<212> TYPE: PRT
<213> ORGANISM: Pseudomonas sp. CF600

<400> SEQUENCE: 10

Met Pro Ile Lys Tyr Lys Pro Glu Ile Arg His Ser Asp Phe Lys Asp
1               5                   10                  15

Leu Thr Asn Leu Ile His Phe Gln Ser Met Glu Gly Lys Ile Trp Leu
            20                  25                  30

Gly Glu Gln Arg Met Leu Leu Leu Gln Phe Ser Ala Met Ala Ser Phe
        35                  40                  45

Arg Arg Glu Met Val Asn Thr Leu Gly Ile Glu Arg Ala Lys Gly Leu
    50                  55                  60

Phe Leu Arg His Gly Tyr Gln Ser Gly Leu Lys Asp Ala Glu Leu Ala
65                  70                  75                  80

Arg Lys Leu Arg Pro Asn Ala Ser Glu Val Gly Met Phe Leu Ala Gly
                85                  90                  95

Pro Gln Met His Ser Leu Lys Gly Leu Val Lys Val Arg Pro Thr Glu
            100                 105                 110

Leu Asp Ile Asp Met Glu Tyr Gly Arg Phe Tyr Ala Glu Met Glu Trp
        115                 120                 125

Ile Asp Ser Phe Glu Val Glu Ile Cys Gln Thr Asp Leu Gly Gln Met

```
            130                 135                 140
Gln Asp Pro Val Cys Trp Thr Leu Leu Gly Tyr Ala Cys Ala Tyr Ser
145                 150                 155                 160

Ser Ala Phe Met Gly Arg Glu Ile Ile Phe Lys Glu Val Ser Cys Arg
                165                 170                 175

Gly Cys Gly Gly
            180

<210> SEQ ID NO 11
<211> LENGTH: 180
<212> TYPE: PRT
<213> ORGANISM: Pseudomonas sp. CF600

<400> SEQUENCE: 11

Met Pro Ile Lys Tyr Lys Pro Glu Ile Gln His Ser Asp Phe Lys Asp
1               5                  10                  15

Leu Thr Asn Leu Ile His Phe Gln Ser Met Glu Gly Lys Ile Trp Leu
                20                  25                  30

Gly Glu Gln Arg Met Leu Leu Gln Phe Ser Ala Met Ala Ser Phe
            35                  40                  45

Arg Arg Glu Met Val Asn Thr Leu Gly Val Glu Arg Thr Lys Gly Leu
50                  55                  60

Phe Leu Arg His Gly Tyr Gln Ser Gly Leu Lys Asp Ala Glu Leu Ala
65                  70                  75                  80

Arg Lys Leu Arg Pro Asn Ala Ser Glu Val Gly Met Phe Leu Ala Gly
                85                  90                  95

Pro Gln Met His Ser Leu Lys Gly Leu Val Lys Val Arg Pro Thr Glu
            100                 105                 110

Leu Asp Ile Asp Lys Glu Tyr Gly Arg Phe Tyr Ala Glu Met Glu Trp
        115                 120                 125

Ile Asp Ser Phe Glu Val Glu Ile Cys Gln Thr Asp Leu Gly Gln Met
130                 135                 140

Gln Gly Pro Val Cys Trp Thr Leu Leu Gly Tyr Ala Cys Ala Tyr Ser
145                 150                 155                 160

Ser Ala Phe Met Gly Arg Glu Ile Ile Phe Lys Glu Val Ser Cys Arg
                165                 170                 175

Gly Cys Gly Gly
            180

<210> SEQ ID NO 12
<211> LENGTH: 180
<212> TYPE: PRT
<213> ORGANISM: Pseudomonas sp. CF600

<400> SEQUENCE: 12

Met Pro Ile Lys Tyr Lys Pro Glu Ile Gln His Ser Asp Phe Lys Asp
1               5                  10                  15

Leu Thr Asn Leu Ile His Pro Gln Ser Met Glu Gly Lys Ile Trp Leu
                20                  25                  30

Gly Glu Gln Arg Met Leu Leu Gln Phe Ser Ala Met Ala Ser Phe
            35                  40                  45

Arg Arg Glu Met Val Asn Thr Leu Gly Ile Glu Arg Ala Lys Gly Leu
50                  55                  60

Phe Leu Arg His Gly Tyr Gln Ser Gly Leu Lys Asp Ala Glu Leu Ala
65                  70                  75                  80

Arg Lys Leu Arg Pro Asn Ala Ser Glu Val Gly Met Phe Leu Ala Gly
```

```
                    85                  90                  95
Pro Gln Met His Ser Leu Lys Gly Leu Val Lys Val Arg Pro Thr Glu
            100                 105                 110
Leu Asp Ile Gly Arg Glu Tyr Gly Arg Phe Tyr Ala Glu Met Glu Trp
            115                 120                 125
Ile Asp Ser Pro Glu Val Glu Ile Cys Gln Thr Asp Leu Gly Gln Met
        130                 135                 140
Gln Asp Pro Val Cys Trp Thr Leu Leu Gly Tyr Ala Cys Ala Tyr Ser
145                 150                 155                 160
Ser Ala Leu Met Gly Arg Glu Ile Ile His Lys Glu Val Ser Cys Arg
                165                 170                 175
Gly Cys Gly Gly
            180

<210> SEQ ID NO 13
<211> LENGTH: 180
<212> TYPE: PRT
<213> ORGANISM: Pseudomonas sp. CF600

<400> SEQUENCE: 13

Met Pro Ile Lys Tyr Lys Pro Glu Ile Gln His Ser Asp Phe Lys Asp
1               5                   10                  15
Leu Thr Asn Leu Ile His Pro Gln Ser Met Glu Gly Lys Ile Trp Leu
            20                  25                  30
Gly Glu Gln Arg Met Leu Leu Leu Gln Phe Ser Ala Met Ala Ser Phe
        35                  40                  45
Arg Arg Glu Met Val Asn Thr Leu Gly Ile Glu Arg Ala Lys Gly Leu
    50                  55                  60
Phe Leu Arg His Gly Tyr Gln Ser Gly Leu Lys Asp Ala Glu Leu Ala
65                  70                  75                  80
Arg Lys Leu Arg Pro Asn Ala Ser Glu Val Gly Met Phe Leu Ala Gly
                85                  90                  95
Pro Gln Met His Ser Leu Lys Gly Leu Val Lys Val Arg Pro Thr Glu
            100                 105                 110
Leu Asp Ile Asp Lys Glu Tyr Gly Arg Phe Tyr Ala Glu Met Glu Trp
            115                 120                 125
Ile Asp Ser Phe Glu Val Glu Ile Cys Gln Thr Asp Pro Gly Gln Met
        130                 135                 140
Gln Asp Pro Val Cys Trp Thr Leu Leu Gly Tyr Ala Cys Ala Tyr Ser
145                 150                 155                 160
Ser Ala Phe Met Gly Arg Glu Ile Ile Phe Lys Glu Val Ser Cys Arg
                165                 170                 175
Gly Cys Gly Gly
            180

<210> SEQ ID NO 14
<211> LENGTH: 25
<212> TYPE: DNA
<213> ORGANISM: Pseudomonas sp. CF600

<400> SEQUENCE: 14
ccatcgctga attctgcagc aacag                                    25

<210> SEQ ID NO 15
<211> LENGTH: 23
<212> TYPE: DNA
<213> ORGANISM: Pseudomonas sp. CF600
```

```
<400> SEQUENCE: 15
cgcacacgga tccaacgagt gag                                              23

<210> SEQ ID NO 16
<211> LENGTH: 19
<212> TYPE: DNA
<213> ORGANISM: Pseudomonas sp. CF600

<400> SEQUENCE: 16
ccgtcgattg atcatttgg                                                   19

<210> SEQ ID NO 17
<211> LENGTH: 20
<212> TYPE: DNA
<213> ORGANISM: Pseudomonas sp. CF600

<400> SEQUENCE: 17
tgtccatcat attgcgcacg                                                  20
```